United States Patent
Berkels et al.

(10) Patent No.: US 6,581,613 B2
(45) Date of Patent: Jun. 24, 2003

(54) ALKYLPOLYGLUCOSIDE WITH A HIGH DEGREE OF OLIGOMERIZATION

(75) Inventors: Wolfgang Berkels, Bottrop (DE); Burghard Grüning, Essen (DE); Felix Müller, Velbert (DE); Jörg Peggau, Essen (DE)

(73) Assignee: Goldschmidt AG, Goldschidtstrasse (DE)

( * ) Notice: Subject to any disclaimer, the term of this patent is extended or adjusted under 35 U.S.C. 154(b) by 233 days.

(21) Appl. No.: 09/784,266

(22) Filed: Feb. 15, 2001

(65) Prior Publication Data

US 2002/0013253 A1 Jan. 31, 2002

(30) Foreign Application Priority Data

Mar. 3, 2000 (DE) .......................... 100 10 420

(51) Int. Cl.[7] .............................. B08B 3/04; B08B 3/08; C11D 3/37; C11D 7/06
(52) U.S. Cl. ................ 134/22.1; 134/22.17; 134/22.19; 134/25.4; 134/39; 134/40; 134/42; 510/199; 510/218; 510/470
(58) Field of Search ................................. 510/199, 218, 510/470; 134/22.1, 22.17, 22.19, 25.4, 39, 40, 42

(56) References Cited

U.S. PATENT DOCUMENTS

| | | | | |
|---|---|---|---|---|
| H468 H | * | 5/1988 | Malik et al. ................. | 252/542 |
| 5,996,692 A | * | 12/1999 | Chan et al. .................. | 166/263 |
| 6,194,371 B1 | * | 2/2001 | Donovan et al. ........... | 510/396 |
| 2002/0013253 A1 | * | 1/2002 | Berkels et al. .............. | 510/470 |

FOREIGN PATENT DOCUMENTS

| | | | |
|---|---|---|---|
| DE | 196 07 753 A1 | 9/1997 | ............ C11D/3/22 |
| EP | 1130026 A2 * | 9/2001 | ............ C07H/15/04 |
| WO | WO 99/21948 | 5/1999 | ............ C11D/1/66 |

* cited by examiner

Primary Examiner—Yogendra N. Gupta
Assistant Examiner—Brian P. Mruk
(74) Attorney, Agent, or Firm—Scully, Scott, Murphy & Presser

(57) ABSTRACT

The present invention provides a defined alkylpolyglucoside having a degree of oligomerization of at least 1.7 to 3 and an alkyl radical comprising 8 carbon atoms, and mixtures of this alkylpolyglucoside with further alkylpolyglucosides, as cleaner concentrate. The present invention also relates to compositions which include the defined alkylpolyglucoside and a concentrated alkali metal hydroxide solution as well as a method of using the composition as a cleaner.

7 Claims, No Drawings

ALKYLPOLYGLUCOSIDE WITH A HIGH DEGREE OF OLIGOMERIZATION

FIELD OF THE INVENTION

The present invention relates to a defined alkylpolyglucoside, to mixtures of this alkylpolyglucoside with other alkylpolyglucosides, and to the use of these alkylpolyglucosides as a cleaner concentrate.

BACKGROUND OF THE INVENTION

Cleaning in place procedure is usually carried out using highly concentrated industrial alkaline hydroxide solutions, for example, 50% strength by weight sodium hydroxide solution or 45% strength by weight potassium hydroxide solution. In the corresponding works, for example, a brewery or dairy, this cleaner concentrate is diluted to customary use concentrations for the appropriate application. To increase the cleaning performance, further surfactants are customarily used.

From WO 99/21948, it is known that alkylpolyglucosides with hexyl substitution are stable in concentrated alkali metal hydroxide solutions. Thus, in the table on Page 8 of WO '948, an n-hexylglucoside is described which gave a clear solution even in 40% strength by weight sodium hydroxide solution at a concentration of 7.5%. Data on the degree of oligomerization (DP) are not contained in this publication.

The product described in United States Statutory Invention Registration H171 is likewise unsuitable for combination with highly concentrated alkali metal hydroxide solutions.

DE-A-196 07 753 describes alkylpolyglucosides with a high degree of oligomerization as high-performance surfactants for liquid detergents and cleaners. It is described in the '753 publication how suitable alkylpolyglucosides are accessible by processing fatty alcohols and glucose in a molar ratio of 3:1 to 10:1 at temperatures in the range from 90° to 120° C. in an acid-catalyzed acetalation with continuous removal of the water of reaction by distillation to give alkyloligoglucosides with a low degree of oligomerization (<1.6), and, following termination of the reaction, neutralizing the acidic catalyst to 0 to 90 mol %.

Following removal of such an amount of unreacted fatty alcohol, which regulates the molar ratio of the remaining fatty alcohol and glucose, based on the starting amount, to 1:1 to 3:1, the reaction mixture is subjected to postpolymerization at temperatures in the range from 90° to 120° C.

Following neutralization of the remaining amount of the acidic catalyst and removal of the unreacted fatty alcohol, alkyloligoglucosides are obtained which have a degree of oligomerization in the range from 1.6 to 2.5, in particular 1.6 to 2, without the products being burdened by too high a polyglucose content or inadequate color quality. In the '753 publication, it was possible to reduce the polyglucose fraction to below 5%.

Typical examples of fatty alcohols which may be used as starting material in the process are caproic alcohol, caprylic alcohol, 2-ethylhexyl alcohol, capric alcohol, lauryl alcohol, isotridecyl alcohol, myristyl alcohol, cetyl alcohol, stearyl alcohol, isostearyl alcohol and behenyl alcohol, and mixtures thereof, which are produced, for example, during high-pressure hydrogenation of technical-grade methyl esters based on fats and oils or aldehydes from the Roelen oxo synthesis, and as monomer fraction during the dimerization of unsaturated fatty alcohols.

Particularly preferred technical-grade fatty alcohols are those having 8 to 10, or 12 to 18 carbon atoms, in particular hydrogenated forerun, coconut, palm, palm kernel or tallow fatty alcohol.

The acidic catalysts used are, in particular, sulfuric acid, alkylsulfuric monoesters, alkyklbenzenesulfonic acid, such as, for example, p-toluenesulfonic acid or dodecylbenzenesulfonic acid and sulfosuccinic acid. The amounts used are usually in the range from 0.1 to 5% by weight, preferably 0.5 to 2% by weight, based on the substances used.

However, the surfactants specifically disclosed in the '753 publication are not suitable for highly concentrated alkaline cleaner concentrates.

Accordingly, there is a need to provide a highly stable polyalkylglucoside which is stable in commercially available concentrated technical-grade alkali metal hydroxide solutions and at the same time has good emulsifying power.

SUMMARY OF THE INVENTION

The above object is achieved according to the present invention by providing an alkylpolyglucoside having a degree of oligomerization (DP) of at least 1.7 to 3, where the alkyl radical comprises 8 carbon atoms. Thus, according to the present invention, ethylhexylglucoside with a degree of oligomerization in the range from 1.7 to 3 is described.

DETAILED DESCRIPTION OF THE INVENTION

Surprisingly, it has been found that the alkylpolyglucoside of the present invention has long-term stability even in highly concentrated alkali metal hydroxide solutions based on sodium hydroxide solution or potassium hydroxide solution and does not lead to precipitations. The emulsifying power is also good in dilute alkaline cleaner solutions.

The alkylpolyglucoside according to the present invention is obtainable by a process described in detail in DE-A- 196 07 753. In this respect, the entire contents of the '753 publication are incorporated herein by reference.

In a preferred embodiment of the present invention, the alkylpolyglucoside according to the present invention has a degree of oligomerization (DP) of from 1.85 to 2.5.

In the prior art, it is known to use cleaner concentrates based on alkylpolyglucosides having alkyl radicals in which the number of carbon atoms in the alkyl radical is other than 8 (see, for example, DE-A-196 07 753). Thus, the prior art discloses alkylpolyglucosides having an alkyl radical which comprises, in particular, 6 to 24 carbon atoms. These alkylpolyglucosides known per se can be used for the purposes of the present invention in combination with ethylhexylglucoside. For the purposes of the present invention, particular preference is therefore given to mixtures of alkylpolyglucosides of different origin than the ethylhexylglucoside, the weight ratio of the ethylhexylglucoside to the other alkylpolyglucosides being adjusted such that at least 50% by weight of the alkylpolyglucoside consist of ethylhexylglucoside.

To use the alkylpolyglucoside according to the present invention and mixtures of the inventive alkylpolyglucoside with other alkylpolyglucosides, the inventive alkylpolyglucosides are admixed with concentrated technical-grade alkali metal hydroxide solution. Commercially available technical-grade concentrated alkali metal hydroxide solutions include, for example, 50% by weight of NaOH or 45% by weight of KOH in water.

For the purposes of the present invention, particular preference is therefore given to mixtures of one or more of said alkylpolyglucosides with technical-grade concentrated alkali metal hydroxide solutions, said mixtures comprising 50 to 99.9% by weight of concentrated alkali metal hydroxide solutions and 0.1 to 50% by weight of the alkylpolyglucosides. For the purposes of the present invention, particular preference is given to corresponding mixtures which comprise 90 to 99.9% by weight of technical-grade concentrated alkali metal hydroxide solutions and 0.1 to 10% by weight of the alkylpolyglucosides.

For the purposes of the present invention, particular preference is given to the above-mentioned cleaner concentrate for the cleaning of surfaces in breweries and dairies.

The alkylpolyglucoside according to the invention is considerably less foaming, although the surface activity is not adversely affected.

The following examples are given to illustrate the present invention as well as show some advantages that are obtained therefrom.

Working Examples:

EXAMPLE 1

Comparative Examples 1 to 7

The alkylpolyglucosides (APG) given in Table 1 below were prepared analogously to DE 196 07 753 A1:

TABLE 1

| Examples: | Compound: | Degree of oligomerization: |
|---|---|---|
| Example 1 | EthylhexylPG | approx. 2.0 |
| Comparative example 1 | EthylhexylPG | approx. 1.1 |
| Comparative example 2 | EthylhexylPG | approx. 1.3 |
| Comparative example 3 | EthylhexylPG | approx. 1.6 |
| Comparative example 4 | Ethylhexyl-/Decyl-PG | approx. 1.5 |
| Comparative example 5 | Octyl-decyl-PG | approx. 1.6 |
| Comparative example 6 | Octyl-decyl-PG | approx. 1.6 |
| Comparative example 7 | Octyl-decyl-PG* | approx. 1.6 |

*As in US 1985-801170

In Table 2 below, the solubility behavior of the above-described alkylpolyglucosides in concentrated aqueous sodium hydroxide solution was investigated:

TABLE 2

| | Dissolved in % by weight of NaOH | | | | | | |
|---|---|---|---|---|---|---|---|
| Examples: | 15 | 20 | 25 | 30 | 35 | 40 | 50 |
| Example 1 | + | + | + | + | + | + | + |
| Comparative example 1 | + | − | − | − | − | − | − |
| Comparative example 2 | + | + | − | − | − | − | − |
| Comparative example 3 | + | + | + | − | − | − | − |
| Comparative example 4 | + | + | + | + | + | ± | − |
| Comparative example 5 | + | + | ± | − | − | − | − |
| Comparative example 6 | + | + | + | − | − | − | − |
| Comparative example 7 | + | + | + | − | − | − | − |

The solubility in concentrated potassium hydroxide solution was also determined in an identical manner. The results are given here in Table 3:

TABLE 3

| | Dissolved in % by weight of KOH | | | | | | |
|---|---|---|---|---|---|---|---|
| Examples: | 15 | 20 | 25 | 30 | 35 | 40 | 45 |
| Example 1 | + | + | + | + | + | + | + |
| Comparative example 4 | + | + | + | + | + | + | ± |

In a further test series, the emulsifiability of the above-mentioned alkylpolyglucosides in a dilution of 1.0 g/l in olive oil was determined:

The emulsifying power was determined by preparing a 1:1 mixture with water and commercially available olive oil. 0.05% of the alkylpolyglucosides were added thereto and then mixed with vigorous shaking. The separation of oil was observed at different time intervals. The lower the oil separation, the more efficient the surfactant.

Using the alkylpolyglucosides of Comparative examples 1 to 3 and 5 to 7, no emulsions could be obtained.

Table 4 below shows the data obtained:

TABLE 4

| | % oil seperation | | | |
|---|---|---|---|---|
| Examples | 30 min | 1 h | 2 h | 3 h |
| Example 1 | 2 | 4 | 8 | 12 |
| Comparative example 4 | 1 | 6 | 10 | 20 |

The table below gives formulations of the alkaline cleaners with a maximum NaOH concentration:

TABLE 5

| Examples | NaOH 50% strength | Gluconic acid 50% strength | Amount of the APG* | Water |
|---|---|---|---|---|
| Example 1* | 80 | 10.0 | 5.0 | — |
| Comparative example 4* | 70 | 10.0 | 5.0 | ad 100 |
| Comparative example 6 | 60 | 10.0 | 5.0 | ad 100 |
| Comparative example 7 | 60 | 10.0 | 5.0 | ad 100 |

*per 100% active substance

The table below gives the emulsifiability of alkaline cleaners in olive oil in a 1% strength dilution (comprises 0.5 g/l of the APG in the solution tested):

TABLE 6

| | % water seperation | | | |
|---|---|---|---|---|
| Examples | 30 min | 1 h | 3 h | 24 h |
| Example 1 | 0 | 0 | 8 | 40 |
| Comparative example 4 | 0 | 0 | 12 | 54 |
| Comparative example 6 | 0 | 0 | 10 | 50 |
| Comparative example 7 | 0 | 0 | 14 | 56 |

The table below gives the emulsifiability of alkaline cleaners in olive oil in a 0.5% strength dilution (comprises 0.25 g/l of the APG in the solution tested):

TABLE 7

| | % water seperation | | | |
|---|---|---|---|---|
| Examples | 30 min | 1 h | 3 h | 24 h |
| Example 1 | 0 | 1 | 8 | 40 |
| Comparative example 4 | 0 | 2 | 8 | 40 |

The table below gives the emulsifiability of alkaline cleaners in olive oil in a 0.25% strength dilution (comprises 0.125 g/l of he APG in the solution tested):

TABLE 8

| | % water seperation | | | |
|---|---|---|---|---|
| Examples | 30 min | 1 h | 3 h | 24 h |
| Example 1 | 0 | 1 | 6 | 30 |
| Comparative example 4 | 0 | 2 | 6 | 30 |

The table below gives the emulsifiability of alkaline cleaners in olive oil in a 0.1% strength dilution (comprises 0.05 g/l of The APG in the solution tested):

TABLE 9

| Examples | % water seperation | | | |
|---|---|---|---|---|
| | 30 min | 1 h | 3 h | 24 h |
| Example 1 | 0 | 2 | 6 | 0 |
| Comparative example 4 | 0 | 2 | 6 | 4 ml oil |

The table below gives the foaming behavior (DIN 53902) of 1.0 g/l of ethylhexylPG of varying degrees of DP:

The foaming ability was determined in accordance with DIN 53902 Part 1, the procedure here being the perforated-plate impact procedure in the manual impact method.

A measuring cylinder (500 ml in size) with cm graduations was charged with 250 ml of surfactant solution; this corresponded to a liquid level of 14 cm. The perforated plunger (disk diameter 45 mm with 12 holes per 5 mm) was placed onto the cylinder and 20 uniform plunges were made. The foam produced as a result was given in cm of foam height. The value directly after the plunging was given as the total height (liquid and foam), but in the case of the values for 30, 60 and 120 seconds, only the actual foam height was given.

TABLE 10

| Examples | Foam height (cm) | | | |
|---|---|---|---|---|
| | Initially | 30" | 60" | 120" |
| Example 1 | 10 | 1.5 | 1 | 1 |
| Comparative example 1 | 14 | 2 | 1 | 1 |
| Comparative example 2 | 13 | 2 | 1 | 1 |
| Comparative example 3 | 12 | 1.5 | 1 | 1 |

The table below gives the foaming behavior (DIN 53902) of alkaline cleaners containing the APG:

TABLE 11

| Examples | Conc. | Foam height (cm) | | | |
|---|---|---|---|---|---|
| | | Initially | 30" | 60" | 120" |
| Example 1* | 0.50% | 10 | 2 | 1 | 1 |
| Comparative example 4* | 0.50% | 13 | 11 | 10 | 10 |
| Example 1* | 0.25% | 8 | 1 | 0.5 | 0.5 |
| Comparative example 4* | 0.25% | 9 | 7 | 6 | 6 |
| Example 1* | 0.10% | 5 | 0 | 0 | 0 |
| Comparative example 4* | 0.10% | 7 | 5 | 4 | 3.5 |

*refers to the formulations according to Table 5

The table below gives the surface tension of 1.0 g/l of ethylhexylPG of varying degrees of DP:

A K10ST digital tensiometer from Krüss was used. The measurement body used was a ring, in accordance with Du Nouy.

The platinum ring was immersed into the liquid to be investigated and then drawn out again. The force required to pull the ring through the surface was measured.

TABLE 12

| Examples | Surface tension (mN/cm) |
|---|---|
| Example 1 | 33 |
| Comparative example 1 | 34 |
| Comparative example 2 | 33 |
| Comparative example 3 | 32 |

The table below gives the surface tension of alkaline cleaners containing the APG:

TABLE 13

| Examples | Conc. | APG active ingredient content | Surface tension (mN/cm) |
|---|---|---|---|
| Example 1* | 0.50% | 0.25 g/l | 35 |
| Comparative example 4* | 0.50% | 0.25 g/l | 28 |
| Example 1* | 0.25% | 0.125 g/l | 43 |
| Comparative example 4* | 0.25% | 0.125 g/l | 30 |
| Example 1* | 0.10% | 0.05 g/l | 47 |
| Comparative example 4* | 0.10% | 0.05 g/l | 34 |

*refers to formulations according to Table 5

While the present invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms and details described and illustrated but fall within the scope of the appended claims.

Having thus described our invention in detail, what we claim as new and desire to secure by the Letters Patent is:

1. A composition comprising a mixture of 0.1 to 10% by weight of one or more alkylpolyglucosides having a degree of oligomerization (DP) between 1.7 to 3, where the alkyl radical comprises 8 carbon atoms; and 90 to 99.9% by weight of a concentrated alkali metal hydroxide solution.

2. The composition of claim 1 wherein the composition further comprises at least one additional alkylpolyglucoside having an alkyl radical which comprises 6 to 24 carbon atoms.

3. The composition of claim 2 wherein the weight ratio of the alkylpolyglucoside having 8 carbon atoms to the additional alkylpolyglucoside having 6 to 24 carbon atoms is adjusted such that at least 50% by weight of the alkylpolyglucosides comprise ethylhexylglucoside.

4. The composition of claim 1 where said alkylpolyglucoside having 8 carbon atoms has a degree of oligomerization of 1.85 to 2.5.

5. A method for industrial cleaning of surfaces comprising: applying a composition comprising 0.1 to 10% by weight of an alkylpolyglucoside having a degree of oligomerization between 1.7 to 3, wherein the alkyl radical comprises 8 carbon atoms; and 90 to 99.9% by weight of a concentrated alkali metal hydroxide solution to a surface requiring cleaning.

6. The method of claim 5 wherein the composition further comprises at least one additional alkylpolyglucoside having an alkyl radical which comprises 6 to 24 carbon atoms.

7. The method of claim 6 wherein the weight ratio of the alkylpolyglucoside having 8 carbon atoms to the additional alkylpolyglucoside having 6 to 24 carbon atoms is adjusted such that at least 50% by weight of the alkylpolyglucosides comprise ethylhexylglucoside.

* * * * *